(12) United States Patent
Conklin et al.

(10) Patent No.: US 9,936,947 B2
(45) Date of Patent: Apr. 10, 2018

(54) SYSTEMS FOR DEPLOYING KNOTLESS SUTURE ANCHORING CLAMPS

(71) Applicant: Edwards Lifesciences Corporation, Irvine, CA (US)

(72) Inventors: Brian S. Conklin, Orange, CA (US); Louis A. Campbell, Santa Ana, CA (US); Salvador Marquez, Foothill Ranch, CA (US); Donald E. Bobo, Jr., Santa Ana, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 15/362,529

(22) Filed: Nov. 28, 2016

(65) Prior Publication Data
US 2017/0071600 A1 Mar. 16, 2017

Related U.S. Application Data

(63) Continuation of application No. 14/797,112, filed on Jul. 11, 2015, now Pat. No. 9,504,466, which is a (Continued)

(51) Int. Cl.
*A61B 17/04* (2006.01)
*A61F 2/24* (2006.01)

(52) U.S. Cl.
CPC ...... *A61B 17/0487* (2013.01); *A61B 17/0401* (2013.01); *A61F 2/24* (2013.01);
(Continued)

(58) Field of Classification Search
CPC . A61B 17/04; A61B 17/0401; A61B 17/0487; A61B 17/122; A61B 17/1227;
(Continued)

(56) References Cited

U.S. PATENT DOCUMENTS

| 1,243,105 A | 10/1917 | Richardson |
| 3,753,438 A | 8/1973 | Wood et al. |

(Continued)

FOREIGN PATENT DOCUMENTS

| EP | 0519703 A1 | 12/1992 |
| EP | 0635241 A2 | 1/1995 |
| EP | 0967940 A1 | 1/2000 |

OTHER PUBLICATIONS

International Search Report from corresponding PCT case No. PCT/US2012070547 dated Dec. 12, 2015.

*Primary Examiner* — Victor Nguyen
(74) *Attorney, Agent, or Firm* — Guy L. Cumberbatch; Pui Tong Ho

(57) ABSTRACT

Suture locking clamps for securing prostheses such as heart valves or annuloplasty rings with sutures and without knots improve the ease of implantation. The clamps have opposed clamp halves separated by a slot opening to one side and surrounded by a biasing member such as one or more C-clip springs. Sutures pass laterally into the slot which is held open by a retention member positioned between the clamp halves. The locking clamp slides along the sutures into position, the tension of the sutures is adjusted, and the retention member removed to allow the biasing member to clamp the sutures between the clamp halves. A delivery tool used to deliver and deploy the locking clamps contains a number of clamps within a delivery tube in a stack and bonded together for safety and a common retention member. The tool has a longitudinal channel on one side for entry of sutures.

19 Claims, 7 Drawing Sheets

Related U.S. Application Data continuation of application No. 13/920,983, filed on Jun. 18, 2013, now Pat. No. 9,078,652, which is a continuation-in-part of application No. 13/719,009, filed on Dec. 18, 2012, now Pat. No. 9,078,645.

(60) Provisional application No. 61/639,759, filed on Apr. 27, 2012, provisional application No. 61/577,255, filed on Dec. 19, 2011.

(52) U.S. Cl.
CPC .......... *A61F 2/2409* (2013.01); *A61F 2/2442* (2013.01); *A61B 2017/0404* (2013.01); *A61B 2017/0409* (2013.01); *A61B 2017/0414* (2013.01); *A61B 2017/0416* (2013.01); *A61B 2017/0464* (2013.01); *A61B 2017/0488* (2013.01); *A61B 2017/0496* (2013.01)

(58) Field of Classification Search
CPC .......... A61B 17/128; A61B 2017/0488; A61B 2017/0404; A61B 2017/0496
See application file for complete search history.

(56) References Cited

U.S. PATENT DOCUMENTS

| | | |
|---|---|---|
| 3,857,396 A | 12/1974 | Hardwick |
| 3,910,281 A | 10/1975 | Kletschka et al. |
| 3,976,079 A | 8/1976 | Samuels et al. |
| 3,988,810 A | 11/1976 | Emery |
| 4,291,698 A | 9/1981 | Fuchs et al. |
| 4,387,489 A | 6/1983 | Dudek |
| 4,548,202 A | 10/1985 | Duncan |
| 4,750,492 A | 6/1988 | Jacobs |
| 4,829,999 A * | 5/1989 | Auth .................. A61M 25/013 24/115 R |
| 4,969,892 A | 11/1990 | Burton et al. |
| 4,997,433 A * | 3/1991 | Goble .................. A61F 2/0811 606/62 |
| 5,070,805 A | 12/1991 | Plante |
| 5,071,431 A | 12/1991 | Sauter et al. |
| 5,078,731 A | 1/1992 | Hayhurst |
| 5,234,449 A | 8/1993 | Bruker et al. |
| 5,282,832 A | 2/1994 | Toso et al. |
| 5,383,905 A | 1/1995 | Golds et al. |
| 5,391,173 A | 2/1995 | Wilk |
| 5,474,572 A | 12/1995 | Hayhurst |
| 5,514,159 A | 5/1996 | Matula et al. |
| 5,520,702 A | 5/1996 | Sauer et al. |
| 5,643,289 A | 7/1997 | Sauer et al. |
| 5,643,295 A | 7/1997 | Yoon |
| 5,645,553 A | 7/1997 | Kolesa et al. |
| 5,669,917 A | 9/1997 | Sauer et al. |
| 5,681,351 A * | 10/1997 | Jamiolkowski .... A61B 17/0487 24/115 M |
| 5,735,877 A | 4/1998 | Pagedas |
| 5,776,188 A | 7/1998 | Shepherd et al. |
| 5,845,645 A | 12/1998 | Bonutti |
| 5,895,393 A | 4/1999 | Pagedas |
| 5,948,001 A | 9/1999 | Larsen |
| 6,015,428 A | 1/2000 | Pagedas |
| 6,039,176 A | 3/2000 | Wright |
| 6,066,160 A | 5/2000 | Colvin et al. |
| 6,074,409 A | 6/2000 | Goldfarb |
| 6,231,592 B1 | 5/2001 | Bonutti et al. |
| 6,241,765 B1 | 6/2001 | Griffin et al. |
| 6,368,334 B1 | 4/2002 | Sauer |
| 6,432,123 B2 | 8/2002 | Schwartz et al. |
| 6,475,230 B1 | 11/2002 | Bonutti et al. |
| 6,537,290 B2 | 3/2003 | Adams et al. |
| 6,589,279 B1 | 7/2003 | Anderson et al. |
| 6,626,930 B1 | 9/2003 | Allen et al. |
| 6,641,592 B1 | 11/2003 | Sauer et al. |
| 6,719,767 B1 | 4/2004 | Kimblad |
| 6,746,457 B2 | 6/2004 | Dana et al. |
| 6,860,890 B2 | 3/2005 | Bachman et al. |
| 6,896,686 B2 | 5/2005 | Weber |
| 7,011,669 B2 | 3/2006 | Kimblad |
| 7,083,628 B2 | 8/2006 | Bachman |
| 7,094,244 B2 | 8/2006 | Schreck |
| 7,112,207 B2 | 9/2006 | Allen et al. |
| 7,235,086 B2 | 6/2007 | Sauer et al. |
| 7,381,210 B2 | 6/2008 | Zarbatany et al. |
| 7,628,797 B2 | 12/2009 | Tieu et al. |
| 7,842,051 B2 | 11/2010 | Dana et al. |
| 7,862,584 B2 | 1/2011 | Lyons et al. |
| 7,875,056 B2 | 1/2011 | Jervis et al. |
| 7,959,674 B2 | 6/2011 | Shu et al. |
| 8,021,421 B2 | 9/2011 | Fogarty et al. |
| 8,100,923 B2 | 1/2012 | Paraschac et al. |
| 8,105,355 B2 | 1/2012 | Page et al. |
| 8,398,657 B2 | 3/2013 | Sauer |
| 8,398,680 B2 | 3/2013 | Sauer et al. |
| 2003/0109922 A1 | 6/2003 | Peterson et al. |
| 2003/0195563 A1 | 10/2003 | Foerster |
| 2006/0004410 A1 | 1/2006 | Nobis et al. |
| 2006/0265010 A1 | 11/2006 | Paraschac et al. |
| 2006/0271105 A1 | 11/2006 | Foerster et al. |
| 2007/0021781 A1 | 1/2007 | Jervis et al. |
| 2007/0088391 A1 | 4/2007 | McAlexander et al. |
| 2007/0270907 A1 | 11/2007 | Stokes |
| 2008/0234729 A1 | 9/2008 | Page et al. |
| 2008/0281356 A1 | 11/2008 | Chau et al. |
| 2009/0082792 A1 | 3/2009 | Koyfman et al. |
| 2010/0023128 A1 | 1/2010 | Malberg |
| 2010/0324597 A1 | 12/2010 | Shikhman |
| 2011/0087242 A1 | 4/2011 | Pribanic et al. |
| 2011/0283514 A1 | 11/2011 | Fogarty et al. |
| 2013/0110164 A1 | 5/2013 | Milazzo et al. |

\* cited by examiner

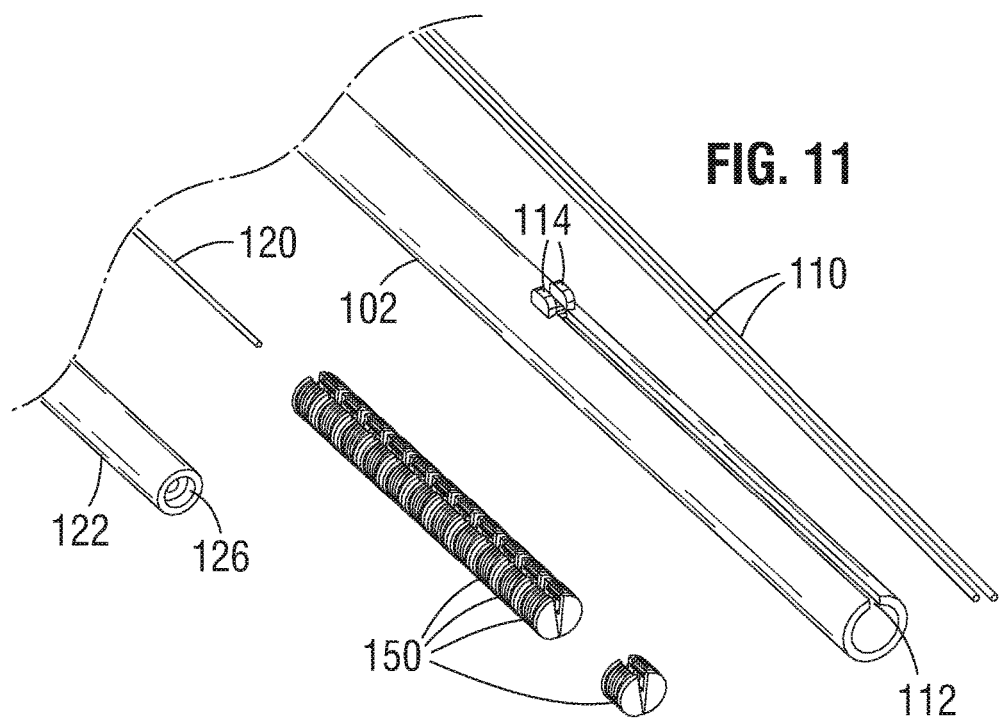
FIG. 11
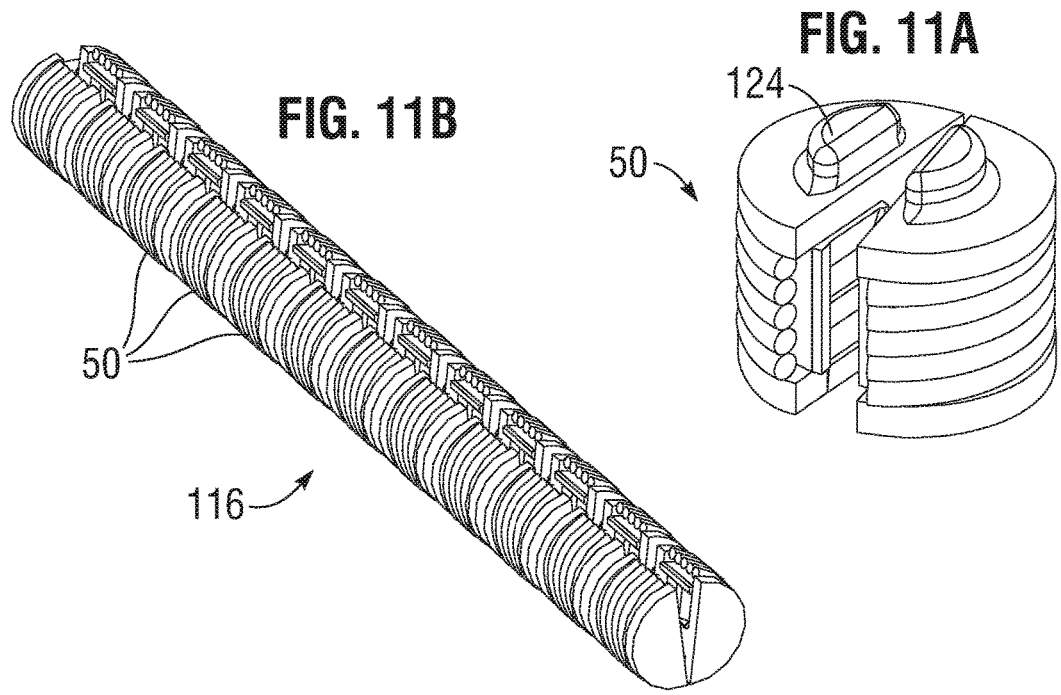
FIG. 11B
FIG. 11A

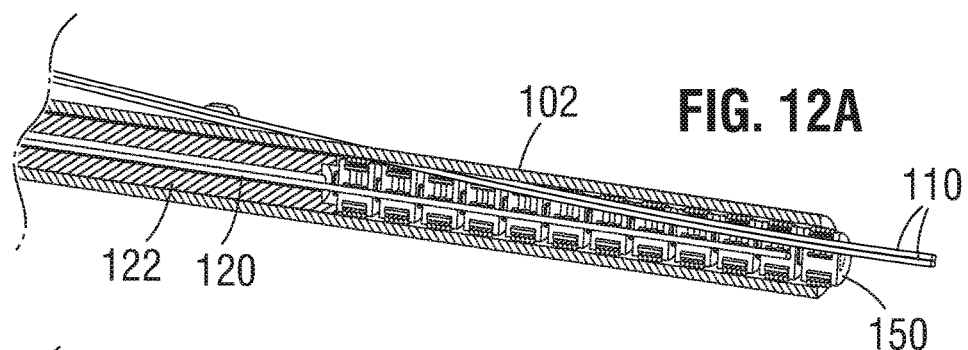
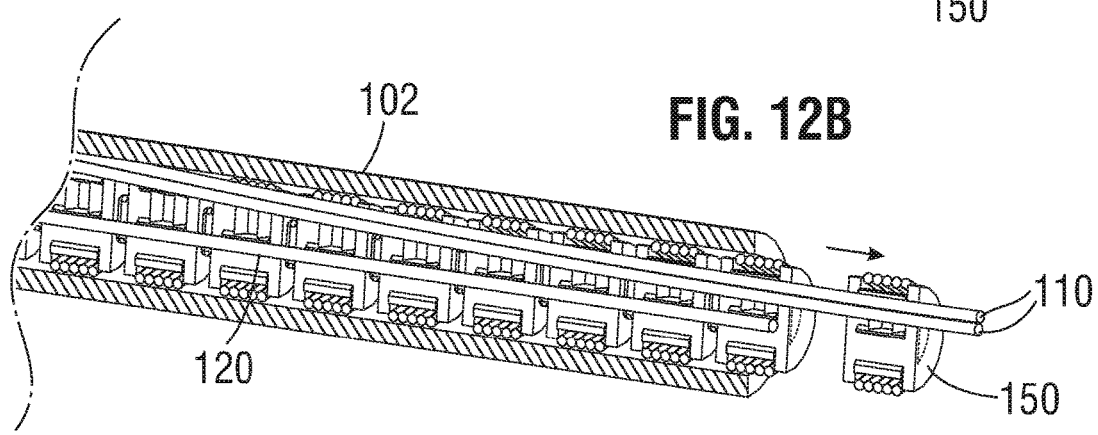
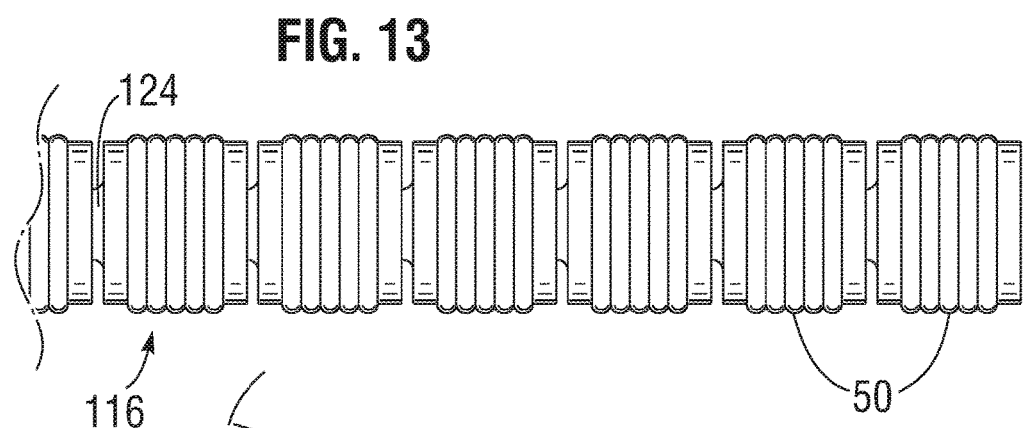
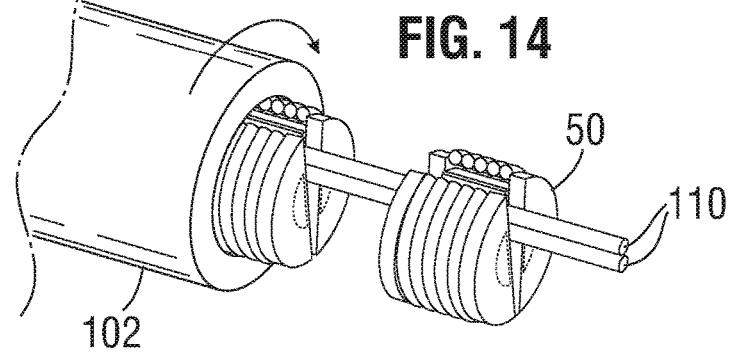

SYSTEMS FOR DEPLOYING KNOTLESS SUTURE ANCHORING CLAMPS

CROSS REFERENCE TO RELATED APPLICATIONS

This application is a continuation of U.S. application Ser. No. 14/797,112 filed Jul. 11, 2015, now U.S. Pat. No. 9,504,466, which is a continuation of U.S. application Ser. No. 13/920,983, filed Jun. 18, 2013, now U.S. Pat. No. 9,078,652, which is a continuation-in-part of U.S. application Ser. No. 13/719,009, filed Dec. 18, 2012, now U.S. Pat. No. 9,078,645, which claims the benefit of U.S. Application Nos. 61/639,759, filed Apr. 27, 2012, and 61/577,255, filed Dec. 19, 2011, all the contents of which are expressly incorporated in their entireties herein.

FIELD OF THE INVENTION

The present invention relates to devices for securing prosthetic implants to soft tissue and, more particularly, to suture clamps and methods for anchoring prostheses inside or near the heart using sutures without knots.

BACKGROUND OF THE INVENTION

Sutures are used for a variety of surgical purposes, such as approximation of tissue and ligation of tissue. When placing sutures, the strand of suture material to be used typically has a needle affixed to one end which is passed (looped) through the tissue to be approximated or ligated, forming a stitch. The stitch is then tensioned appropriately, and the two free ends of the suture loop, the needle end and the non-needle end, are knotted to retain the desired tension in the stitch. Forming knots in suture during open surgery is a simple matter, though time-consuming, but forming knots in sutures during endoscopic surgery can require two surgeons to cooperate in a multi-step process which is performed with multiple instruments to pass the needle and suture back and forth to tie the suture knot.

Within the prior art there exists a need for devices and methods that reduce the time required to secure a heart valve repair prosthesis in place. To repair or replace a defective valve, clinicians can perform traditional open heart surgery or can utilize a minimally invasive or transcatheter technique. Traditional open heart surgery involves administering anesthesia and putting a patient on cardio-pulmonary bypass. A clinician cuts open the chest to access the heart, and then typically excises the defective native valve leaflets leaving the annulus in place. The clinician places sutures in the annulus or other tissue near the heart valve, and threads the free ends of each loop of the sutures through a sewing cuff on the heart valve prosthesis. The heart valve is then "parachuted" into place by sliding it down the suture free ends until it rests on the annulus. The free ends of each suture loop are tied together on the proximal side of the heart valve with multiple knots to prevent the sutures from backing out. Normally, this process entails about 5-10 knots on each of the 12-20 sutures used per implant, which lengthens the time a patient is on cardio-pulmonary bypass and under anesthesia. There is a direct correlation between time spent on bypass and poor outcomes, and thus any reduction in surgical time that a patient undergoes would be beneficial. Implantation of an annuloplasty ring follows a similar procedure except that the native valve is typically left in place. The annuloplasty ring is sutured in place to reshape or repair the valve annulus and improve native heart valve leaflet coaptation.

There also exists a need to make it easier to secure a heart valve repair prosthesis in place. Currently, a clinician must work in the limited space near the heart to tie knots in sutures. This is a cumbersome process that benefits from a clinician of great dexterity and patience. In a minimally invasive surgery the clinician must use tools that can be passed through a small incision, thus making the tying of knots even more difficult. To implant the prosthesis, a clinician makes a small incision in the chest and uses special tools to pass the heart valve repair prosthesis through the incision. An example of a minimally invasive heart valve repair procedure is transapical aortic valve replacement.

Suture locking clamps that eliminate the need to tie knots in order to speed up heart valve replacement are known, as are suture locking devices in general. Suture retainers or locks are used in place of suture knots to prevent passage of a suture end into and through tissue and to maintain the tension applied to the suture material during the suturing procedure. Suture clips and other suture retainers are described in the following publications: U.S. Pat. Nos. 6,066,160, 6,475,230, 7,862,584, 7,875,056, 8,100,923, and 8,105,355.

Despite the existence of knotless suture locking clamps in the art, there is a need for improved clamps that enable accurate tensioning of the suture and are simple to use. Some of the prior clamps utilize a wedge-type system in which a wedge or opposed wedge surfaces are brought together to clamp on the suture. Some of these clamps are susceptible to changes in the magnitude of tension in the suture as they are being locked, either loosening or tightening the suture, while others may work loose if there is no additional mechanism to hold them in place. Some devices such as U.S. Pat. No. 7,862,584 utilize a clamping system having a tortuous path for the suture, which are difficult to thread and also may work loose. Another type of suture locking device shown in U.S. Pat. No. 7,235,086 makes use of a plastically deformable member to capture the suture therein. This device depends on accurate deformation of the clamping member, which might permit the suture to slip loose if insufficiently deformed.

SUMMARY OF THE INVENTION

The present invention provides an improved suture locking clamp for securing heart valve repair or replacement prostheses in or near the heart. The apparatus and methods are particularly well suited for traditional surgery or minimally invasive surgery. The clamps disclosed herein eliminate the need for surgical knots thus reducing surgical time and exposure. Further, the clamps improve the ease of implantation because the clinician need not tie knots in the limited space in and around the heart. Finally, the suture locking clamps are simple to install and their actuation does not affect suture tension.

In accordance with one preferred aspect, the present application provide a system for locking a device on one or more sutures, comprising one or more sutures each having a thickness, a bifurcated clamp member, a biasing member positioned on the outside of the locking clamp, and a retention member positioned between the clamp halves. The locking clamp includes a pair of substantially similar clamp halves each having an exterior surface and an inner surface facing the inner surface of the other clamp half to form a variable-sized side-opening slot therebetween. The clamp halves are connected for movement toward or away from one another while being fixed axially with respect to one another, wherein the suture(s) extend through the slot between the inner surfaces of the clamp halves. The biasing member has a relaxed size that, in the absence of an object in the slot, urges the inner surfaces of the clamp halves together such that the slot has a width smaller than the suture thickness. The retention member acts against the force of the biasing member and has a thickness that maintains the slot width large enough to permit passage of the suture(s) therethrough, wherein removal of the retention member permits the biasing member to urge the inner surfaces of the clamp halves together and clamp the suture(s) therebetween.

The clamp halves may be separate elements, and they may be separate and hinged together or one piece with a living hinge therebetween. In a preferred embodiment, the clamp halves further include outward flanges on opposite axial ends that retain the biasing member in position around the locking clamp. The clamp halves are preferably hinged together on a first circumferential side defining a variable-sized side-opening slot on the side opposite the first circumferential side, and wherein the biasing member comprises a plurality of C-clips arranged around the locking clamp with their free ends located on either side of the variable-sized slot opposite the first circumferential side. In one such embodiment the clamp halves are molded from a single piece of material with a living hinge on the first circumferential side. In a preferred version the inner surfaces of the clamp halves possess features to enhance friction between the clamp halves and the suture, and more preferably the inner surfaces of the clamp halves possess features to create one-way friction between the clamp halves and the suture(s). A maximum radial dimension of the bifurcated clamp member is desirably about 2 mm or less. The clamps may be bonded together in the stack with a weak point therebetween to enable separation of a deployed clamp from the stack.

One aspect of the present application is a system for locking a clamp onto at least one suture having a thickness. The system includes an elongated delivery tool having a delivery tube with a proximal end, a distal end, and a lumen therein, an elongated retention member that extends along the delivery tube, and an actuation trigger on a proximal end of the tool that causes axial displacement of the retention member. A plurality of suture locking clamps are arranged axially in a stack within the delivery tube, each having a bifurcated clamp member including a pair of substantially similar clamp halves with an exterior surface and an inner surface facing the inner surface of the other clamp half. The clamp halves are fixed axially with respect to one another while being connected for movement toward or away from one another to form a variable-sized side-opening slot therebetween perpendicular to the axis sized to receive a suture. Each clamp further includes a biasing member that, in the absence of an object in the slot, urges the inner surfaces of the clamp halves together to clamp onto the suture. The delivery tool retention member is positioned between the clamp halves of each locking clamp against the force of the respective biasing member to maintain the slot width large enough to permit passage of a suture therethrough. Removal of the retention member permits the biasing member to urge the inner surfaces of the clamp halves together and clamp the suture(s) therebetween, and the retention member may be retracted from between the clamp halves of just the distal most clamp to deploy the distal clamp onto the suture. The delivery tube may also have a longitudinal channel commencing at a distal tip and extending a distance axially along the tube, the stack of suture locking clamps being oriented so that their side-opening slots are all aligned with the longitudinal channel to permit side entry of a suture into one or more of the slots.

Another exemplary system for locking a clamp onto at least one suture having a thickness features an elongated delivery tool having a delivery tube with a proximal end, a distal end, and a lumen therein, an elongated retention member that extends along the delivery tube. An actuation trigger on a proximal end of the tool causes axial displacement of the retention member. The delivery tube also has a longitudinal channel commencing at a distal tip and extending a distance axially along the tube. A plurality of suture locking clamps are arranged axially and bonded together in a stack within the delivery tube, adjacent clamps having a weak point of connection therebetween. Each clamp has a variable-sized side-opening slot perpendicular to the axis sized to receive a suture and inner clamping surfaces within the slot to clamp onto a suture. The stack of suture locking clamps are oriented so that their side-opening slots are all aligned with the longitudinal channel to permit side entry of a suture into one or more of the slots. Proximal displacement of the delivery tool retention member deploys at least a distal clamp to clamp the suture(s) therebetween, and the weak point enables easy separation of a deployed clamp from the stack.

In either exemplary system described above, wherein the elongated retention member may comprise a retention cable. The delivery tool may further include a pusher tube located within the delivery tube and in contact with a proximal suture locking clamp in the stack of suture locking clamps. The actuator alternately causes first proximal displacement of the retention member relative to the stack of suture locking clamps and to the pusher tube to activate the distal clamp, and then distal displacement of both the pusher tube and the retention member to eject the distal clamp. Alternatively, the sequence could be first distal displacement of both the pusher tube and the retention member, and then proximal displacement of the retention cable relative to the stack of suture locking clamps and to the pusher tube. Additionally, the delivery tube may be formed of a manually malleable material to enable bending by a surgeon, and the retention member is flexible to avoid impeding bending of the delivery tube.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

The invention will now be explained and other advantages and features will appear with reference to the accompanying schematic drawings wherein:

FIG. 5 shows just the bifurcated clamp member, while

FIG. 11 is an exploded perspective view of components of the side entry suture locking clamp delivery system;

FIG. 11A is an enlarged perspective view of a proximal end of one of the side entry suture locking clamps, while FIG. 11B shows a series of the clamps from a distal end as would be loaded into the delivery system;

FIGS. 12A and 12B are longitudinal sectional views through a distal end of the side entry suture locking clamp delivery system;

FIG. 13 is a side view of a series of the side entry suture locking clamps bonded together;

FIG. 14 is a perspective view of the distal end of a delivery system showing one method of separating a deployed clamp from the stack of clamps.

DETAILED DESCRIPTION OF THE PREFERRED EMBODIMENTS

Various suture locking clamps of the present invention comprise heart valve repair or replacement prosthesis anchors that improve ease of implantation, reduce surgical exposure, and improve prosthesis attachment. It should be appreciated that the principles and aspects of the embodiments disclosed and discussed are also applicable to other types of surgical procedures, namely annuloplasty ring implant for heart valve repair. Furthermore, certain embodiments may also be used in conjunction with other medical devices or other procedures not explicitly disclosed. However, the manner of adapting the embodiments described to various other devices and functionalities will become apparent to those of skill in the art in view of the description that follows.

Figure 1:
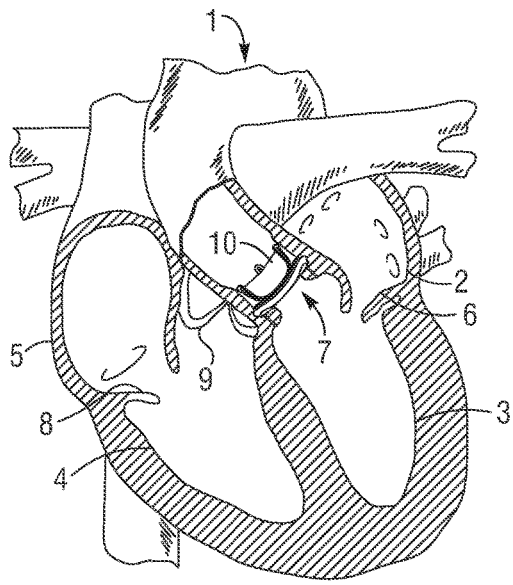
FIG. 1 is a drawing of a prosthetic heart valve implanted in the aortic valve position of a human heart.
Figure 2:
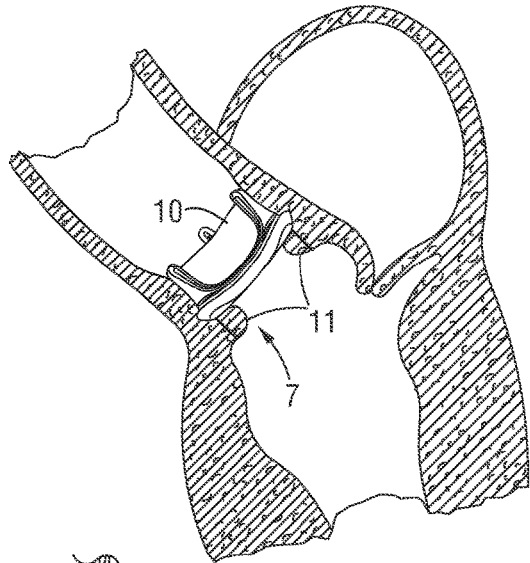
FIG. 2 is an enlarged view of the implanted heart valve of FIG. 1.

A schematic drawing of a surgical prosthetic heart valve implanted in the heart 1 by traditional methods is shown in FIG. 1. The left atrium 2 and the left ventricle 3 are shown separated by the mitral valve 6. The aortic valve 7 is at the outflow end of the left ventricle 3. On the opposite side of the heart, the right atrium 5 and the right ventricle 4 are shown separated by the tricuspid valve 8. The pulmonary valve 9 is at the outflow end of the right ventricle 4. An exemplary surgical prosthetic heart valve 10 is shown implanted in the aortic valve 7 position. An enlarged view of the aortic valve 7 is shown in FIG. 2. The aortic annulus 11 is a fibrous ring extending inward as a ledge into the flow orifice, and can be seen with the prosthetic heart valve 10 sutured in place above it. Prior to valve replacement, the native leaflets extend inward from the annulus 11 and coapt or meet in the flow orifice to permit flow in the outflow direction (up in FIG. 2) and prevent backflow or regurgitation toward the inflow direction (down in FIG. 2).

Figure 3:
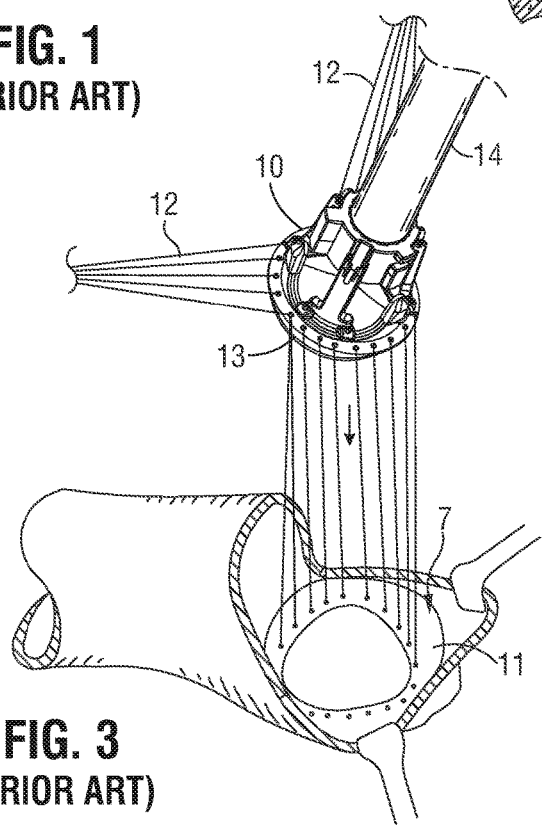
FIG. 3 is a drawing of an intermediate step in the implantation procedure of the heart valve shown in FIG. 1.

FIG. 3 shows one step of the traditional procedure to implant the prosthetic heart valve 10. During implantation, a clinician pre-installs sutures 12 through the annulus 11 of the aortic valve 7. While the heart valve is held on a fixture or holder 14, a clinician can thread the suture 12 free ends through a sewing ring 13 on the prosthetic heart valve 10. Thus, both free ends of each suture 12 extend out of adjacent portions of the sewing ring 13. The valve 10 is then "parachuted" down the array of sutures 12 in the direction shown and pulls the sutures 12 tight so that a seal is formed between the sewing ring 13 and the aortic annulus 11. Next, the clinician ties each suture 12 free end to another free end (typically a loop of one suture strand) securing the prosthetic heart valve 10 in place. Normally this process entails about 5-10 knots per suture and 12-20 sutures are used per implant. The ends of each suture 12 are clipped leaving a suture tail comprised of the suture used to create each knot.

Turning now to the present invention, certain efficiencies when using the suture locking clamps described herein which reduce the procedure time will be explained. In the description that follows, the aortic annulus is used as the implantation site to illustrate the embodiments. The teachings of this invention can also be applied to the mitral, pulmonary, and tricuspid valves; or indeed, other valves in the body, including venous valves. Likewise, unless there is some reason such as space limitations, the suture locking clamps defined herein could be utilized in other surgical contexts.

For purposes of orientation, the upward direction in FIGS. 4-9 shall be termed the proximal direction, while the downward direction shall be the distal direction, corresponding to the typical nomenclature used for a heart valve implantation procedure. Of course, proximal and distal are terms that refer to the position of the surgeon relative to the implant site, and these could be reversed depending on the particular procedure. In any event, an exemplary suture locking clamp 50 defines a central axis therethrough along the proximal-distal orientation.

Figure 4A:
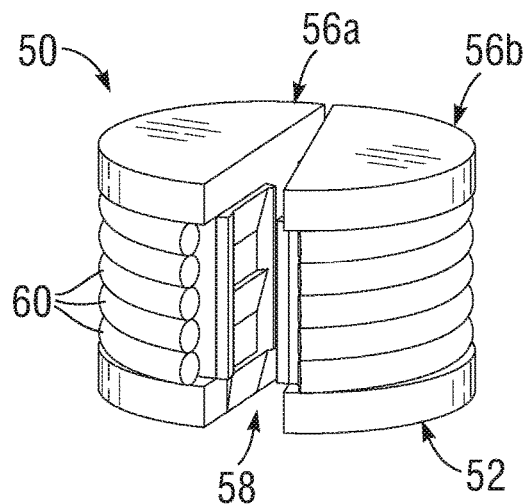
FIGS. 4A and 4B are perspective views of an alternative "side entry" suture locking clamp having a bifurcated clamp member having an axial hinge, as in FIG. 7, and biased together by exterior C-springs.
Figure 4B:
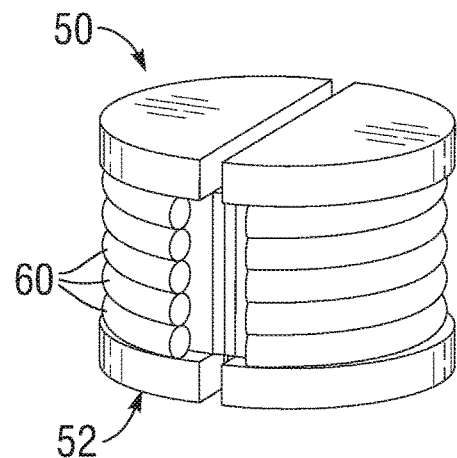
Figure 5:
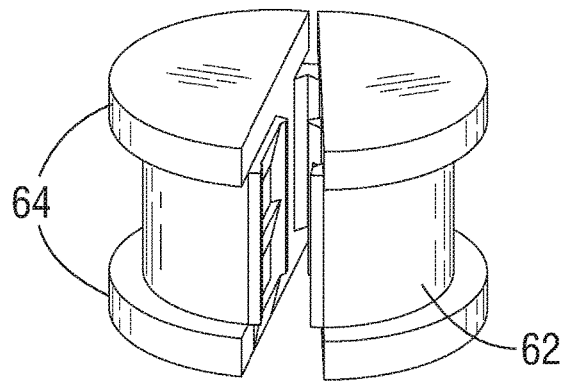
Figure 6:
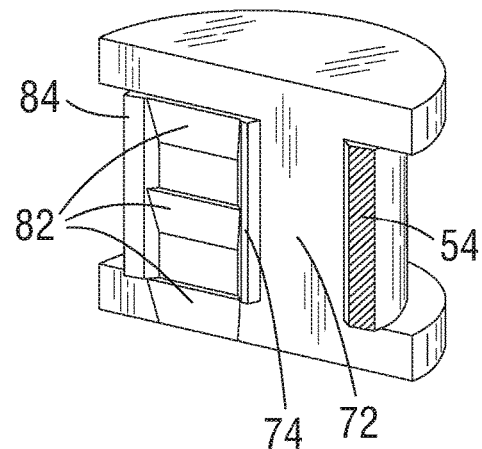
FIG. 6 shows an inner wall structure of one half of the clamp member and FIG. 7 shows one of the C-springs.
Figure 7:
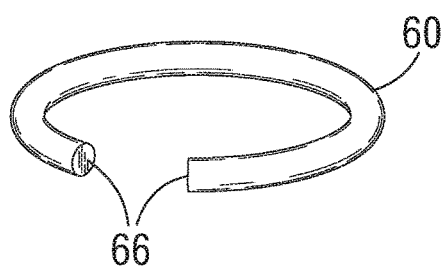

The present application also contemplates a "side-entry" suture locking clamp 50, as shown in FIGS. 4-9 that eliminates the need for tying knots in surgical sutures. The suture locking clamp 50 includes a bifurcated clamp member 52 having an axial hinge 54 (FIG. 6). The clamp member 52 can be manufactured from plastic by molding. The clamp member 52 has two substantially identical halves 56a, 56b separated by a variable-sized slot 58 and biased together by at least one exterior "C" clip 60. The axial hinge 54 is desirably a "living hinge" formed in the molded part along one side so that the halves 56a, 56b can pivot apart to vary the size of the slot 58 and form an opening on the side opposite from the hinge in which sutures can be inserted. Alternatively, a true hinge may be provided between the two halves 56.

One or more of the C-clips 60 are placed around the clamp and sized such that they apply a force which acts to close the clamp member 52 and close or eliminate the slot 58, thus clamping onto sutures that pass through the slot. The C-clip(s) 60 thus provide the biasing member positioned on the outside of the clamp member 52 having a relaxed size that, in the absence of any other object in the slot 58, urges the inner surfaces of the clamp halves 56 together such that the slot has a width smaller than the suture thickness. In an alternative configuration, a section of tube with a slit (forming a "C" in cross section) could replace the array of "C" clips. Indeed, the term, "biasing member" should be understood to refer to one or more elements as described herein.

As seen in FIG. 5, each half 56 includes a semi-cylindrical middle recess 62 between two outwardly-projecting end flanges 64. When the two halves 56 are brought together, they define a spool shape. As seen in FIGS. 4A, 4B, the C-clips 60 are received in the recess 62 with their open ends 66 flanking the variable-sized slot 58 and directly opposed to the hinge 54. The end flanges 64 hold the C-clips 60 in place.

The C-clips 60 would most likely be formed from Nitinol wire, although other materials such as stainless steel should not be excluded. For the exemplary embodiment shown, the C-clips 60 are formed from 0.008" diameter wire and have an outside diameter of 0.079" (2 mm). The illustrated embodiment incorporates five C-clips 60, though additional C-clips 60 could be added to increase the clamping force. Additionally, the clamping force can be increased significantly by small increases in the wire diameter of the C-clips 60. The bending stiffness of a circular wire is proportional to the 4th power of its diameter, and so increasing the wire diameter from only 0.008" to 0.010" increases the clamping force by a factor of 2.4, while an increase to 0.012" would result in a five-fold increase in clamping force. Thus by changing the number of C-clips and their wire diameters, large changes in the clamping force can be realized with minimal impact on the clamp diameter and small changes in clamp height.

FIGS. 8A-8D illustrate a sequence of operation of the side entry suture locking clamp 50. First, the assembled locking clamp 50 includes the aforementioned components as well as a retention pin 70. Prior to use, the two halves 56a, 56b are forced apart so that the retention pin 70 may be inserted into a retention pin channel 72, as seen best in FIG. 6. The retention pin channel 72 is defined between the axial hinge 54 and an axially-oriented retainer rib 74 formed on one or both halves 56 and extending into the slot 58. Release of the two halves 56 permits the C-clips 60 to force the two halves to pivot toward one another and clamp onto the retention pin 70. Preferably, the clamp 50 is pre-assembled by the manufacturer, i.e. the retention pin 70 and C-clips 60 are pre-assembled with the clamp halves 56a, 56b. The presence of the retention pin 70 holds open the two halves 56a, 56b so that the slot 58 widens into the opening opposite the hinge 54 into which one or more sutures 80 can be inserted.

Figure 8A:
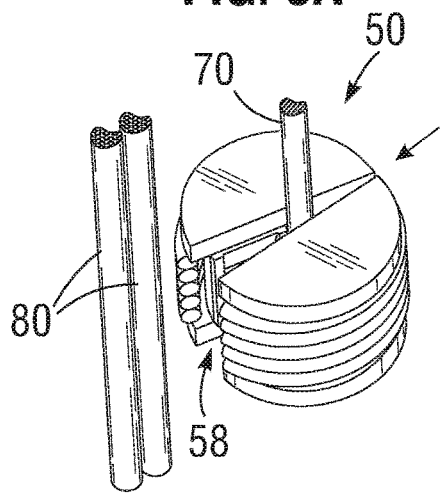
FIGS. 8A-8D are perspective views of a sequence of operation of the side entry suture locking clamp.
Figure 8B:
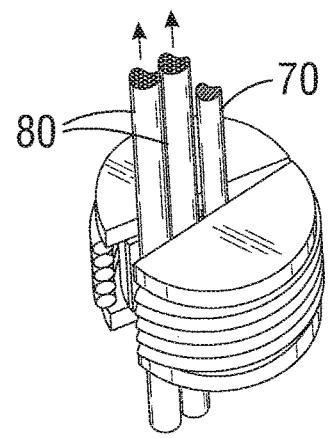
Figure 8C:
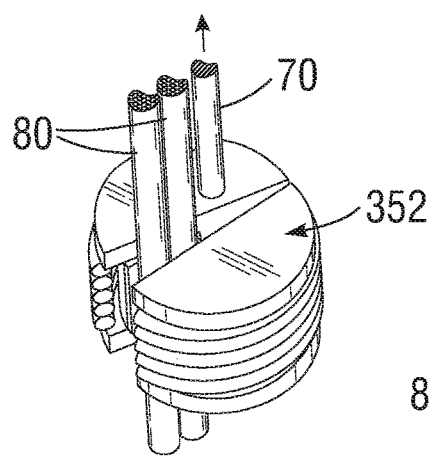
Figure 8D:
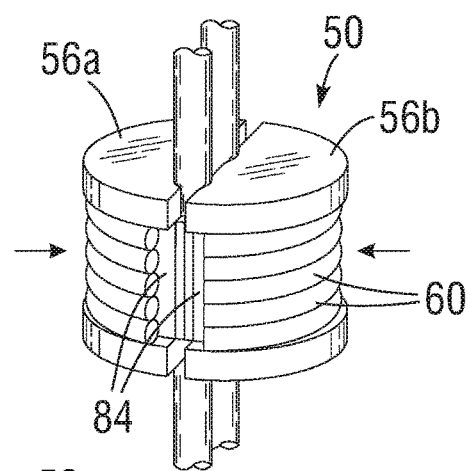

As a first step in the process of deployment, the surgeon laterally displaces one of the suture locking clamps 50 toward one or more sutures 80, as seen in FIG. 8A. As mentioned, the slot 58 defines an opening into which the sutures 80 are received. As seen in FIG. 8B, the surgeon then tensions the sutures 80 while the suture locking clamp 50 is held stationary or pressed (seated) against a stationary substrate, such as the proximal face of a prosthetic heart valve sewing ring or annuloplasty ring. In FIG. 8C, the retention pin 70 is removed, thus allowing the C-clips 60 to force closed the opposite halves 56a, 56b of the clamp member 52, thus clamping the suture(s) 80 therebetween, as seen in FIG. 8D. Because the inner walls of the two halves 56a, 56b are substantially parallel, and parallel to the axis of the C-clips 60, the force on the sutures 80 is radial, thus eliminating any possibility of slippage from axial forces.

In contrast with earlier suture locking clamps, the present clamp relies on strictly radial inward forces to compress the two clamp halves together. Many earlier clamps rely on a wedging action between two surfaces, or between a wedge and surrounding surfaces, thus squeezing sutures between them. This type of fastener relies on an axial force of a spring or other retention member, potentially leading to loosening of the lock if one of the clamping members slips axially. Furthermore, in the process of locking the clamp, the relative sliding of the two retention surfaces may modify the suture tension. In the clamps of the present application, the clamping members apply strictly radial forces, applied instantaneously by removal of the retention pin or clip, which eliminates the risk of altering the suture tension. Furthermore, because the clamps described herein utilize C-clips or other such biasing member to compress radially, much more clamping force is produced for a given size spring as opposed to utilizing the axial force component of a coil spring. This allows the clamps to be advantageously miniaturized compared to those which utilize an axial spring force. A locking clamp which uses an axial spring necessarily requires a minimum spring height, which may detrimentally interfere with certain implant procedures, such as heart valve replacements.

With reference back to FIG. 6, the inner face of one or preferably both of the clamp halves 56a, 56b include a plurality of grip members 82 that help prevent relative movement between the deployed clamp 50 and the sutures 80. More particularly, the grip members 82 prevent relative longitudinal movement between the clamp 50 and sutures 80 in only one direction. For example, the grip members 82 are formed as wedges with a ramp angled in one axial direction, in the illustrated embodiment the wedges are angled upward. Due to their orientation, and after the clamp 50 has been deployed about sutures 80, the sutures would be prevented from moving relatively downward, but could be pulled through upward. That is, even after actuation the clamp 50 can be slid down the sutures 80 against the force of the C-clips 60 without too much difficulty, but not upward. At the same time, the one-way gripping nature of the angled teeth 82 enable the surgeon to increase tension in the portion of the sutures 80 below the suture locking clamp 50 after it has been actuated. It should be understood that the angled teeth 82 are exemplary only, and representative of numerous configurations of enhanced friction within the clamp halves 56. For example, the inner wall may be roughened or provided with bumps, or series of horizontal ridges may be used.

Desirably, both inner faces of the clamp halves 56a, 56b include an axial bar 84 that helps retain the sutures 80 within the slot 58. As seen in FIG. 8D, the bars 34 extends sufficiently inward toward each other so as to close and present a barrier to lateral escape of the sutures 80.

It is important to understand that the C-clips 60 provide a relatively uniform inward biasing force to the two halves 56a, 56b, thus causing the halves to come together with the same force at the top as at the bottom. This helps better retain the sutures 80 since it maximizes the available surface area for gripping with a uniform force. As the C-clips 60 provide an inward biasing force that is axially uniform, they could be replaced with any similar biasing member, such as a sleeve of elastic (e.g., silicone) material, or the like. Furthermore, though the C-clips 60 are advantageous for their relative economy and durability, the inward radial forces they supply around the entire periphery of the locking clamp 50 could be replaced with a biasing member that simply applies compressive forces in the direction perpendicular to the plane between the two halves 56a, 56b. For instance, the locking clamp 50 itself could possess sufficient stiffness to cause the two halves 56a, 56b to come together and retain the sutures 80 without a surrounding spring. In such a configuration, a lock or latch may also be provided to keep the two halves 56a, 56b together once they have clamped the sutures, and prevent outward creep. In short, the clamp 50 includes the two halves 56a, 56b and some sort of biasing force that causes them to come together upon removal of a retention member, as will be clear below.

One particular advantage of the suture locking clamps 50 disclosed herein is their relatively small size, enabling installation of a plurality of the clamps around a heart valve sewing ring without adding significant bulk. For example, both the height and outer diameter of the clamps disclosed herein are desirably about 2 mm or less, and may be as small as 1 mm (i.e., between about 1-2 mm). The initial design shown here is based on 2-0 sutures, which are commonly used in valve replacement procedures. Also, because of the relatively large amount of force a C-clip 60 can generate in the radial direction, a relatively small clip can be used to generate significant clamping forces, thus allowing for a very small clamp.

In a preferred embodiment, the suture locking clamps are made of biocompatible material, including Stainless Steel, Cobalt-Chromium, Nitinol, or the like for the C-clips 60. For the clamp halves, any bio-compatible polymer (e.g., Nylon, Delrin, polypropylene) would be suitable, though metallic materials could also be used. The retention pin 70 is desirably metallic to provide good compressive strength against the force of the C-clips 60. The miniature nature of the clamps render them highly useful for heart valve or annuloplasty ring implant suture anchors.

Another advantage of the suture locking clamps disclosed herein is there low cost of manufacture. For example, the exemplary side entry locking clamps 50 each comprises a molded component and several formed wire C-clips. Even if ten or more of the clamps are required for a procedure, the cost is much less than existing systems.

Further advantages of the clamps disclosed herein are the speed and accessibility of the deployment procedure. Since the clamp is very small it can be delivered from the end of a relatively long and thin delivery shaft where a surgeon's finger may not fit or reach. It is estimated that it takes approximately 15-30 seconds to install each suture locking clamp, including manipulating a delivery tool to capture sutures and activating the clamp. More particularly, the surgeon would first pass the sutures through the side opening of one of the clamps and then advances the clamp down the suture pair to the annulus, pulls the appropriate amount of tension on the sutures, then retracts the retention pin 70 out of the clamp, thereby activating it and allowing it to lock onto the sutures. The suture tails would also be cut at the end of the trigger stroke.

Figure 9:
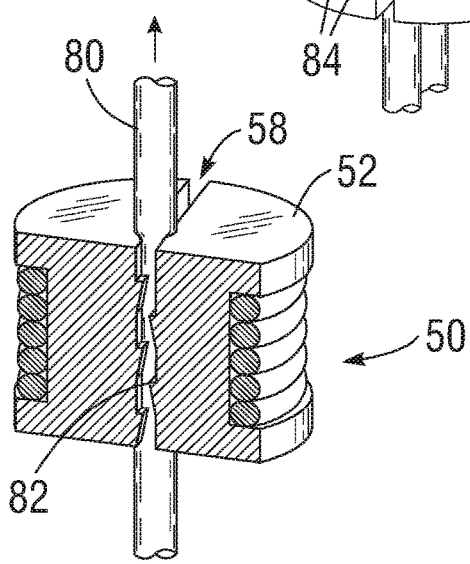
FIG. 9 is a perspective cross sectional view of the side entry suture locking clamp engaging a suture that is pre-attached at one end to the clamp, and showing how the suture(s) can be tensioned further.

FIG. 9 illustrates how the suture(s) 80 can be tensioned further after deployment of the clamp 50. It will be noted that only one suture 80 is shown in this view to emphasize that one or more can be secured by the clamp 50. The individual grip members 82 could be axially offset on the two halves 56 to enhance their frictional hold on the suture(s) 80. In other words, deploying the clamp 50 creates a serpentine path for the suture(s) 80 between the alternating grip members 82. The cross-section of the slot 58 shows the offset suture grips 82, which thus act as a "one way" ratchet that allows for further tensioning of the suture(s) after deployment of the clamp, but resist loosening of the sutures.

Figure 10A:
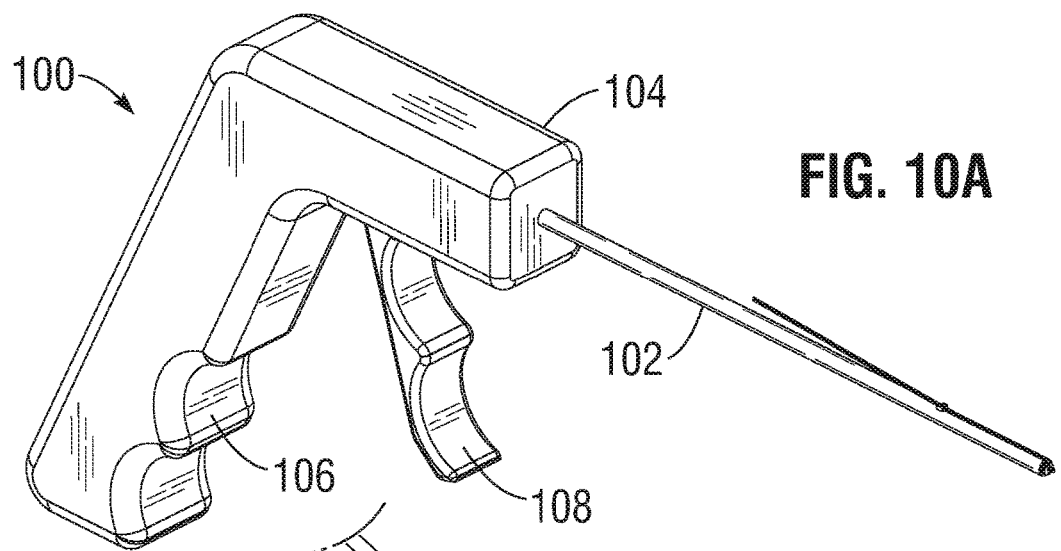
FIGS. 10A-10C are perspective views of an exemplary delivery system for the side entry suture locking clamps described herein.
Figure 10B:
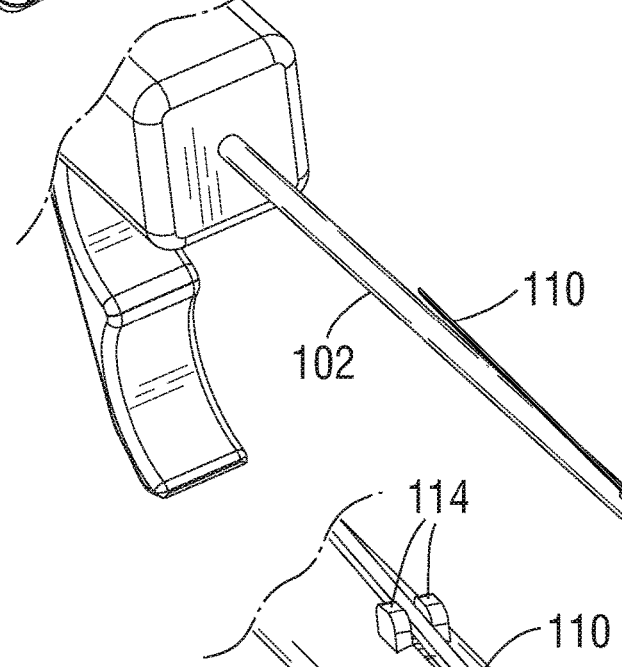
Figure 10C:
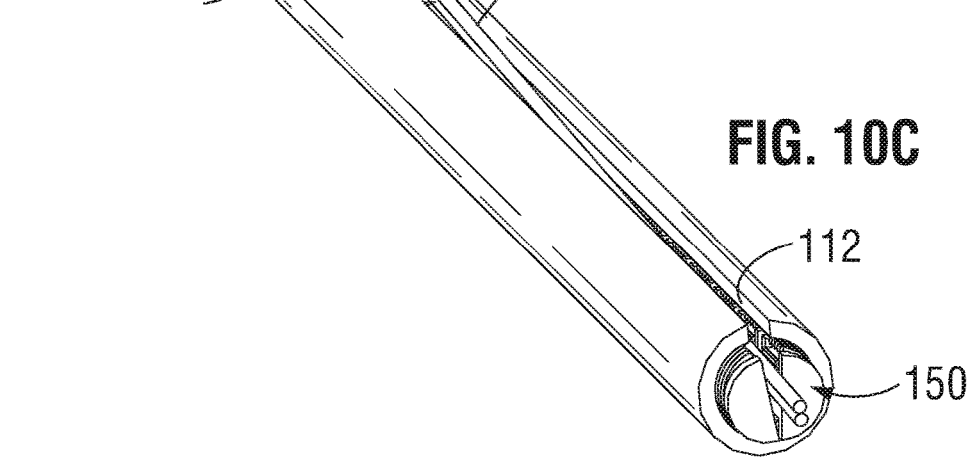

FIGS. 10A-10C illustrate an exemplary delivery system 100 for the side entry suture locking clamps 50 described herein. In the illustrated embodiment, the system 100 is shown as a pistol-like device with a long, malleable shaft 102 extending from a proximal handle 104 having a grip 106 and an actuation trigger 108. Of course, the system can be modified so that the handle 104 is generally aligned along the axis of the shaft 102, with a slider as an actuator, or any other such configuration.

As seen in the detailed view of the distal end of the tubular shaft 102 in FIG. 10C, a pair of sutures 110 are tensioned at a shallow angle with respect to the shaft so as to enter a longitudinal channel 112 on one side of the shaft and into the slot formed in one of the side entry suture locking clamps 50. A pair of guides 114 project outward from the shaft 102 at the proximal termination of the channel 112 to help maintain alignment of the sutures 110 into the channel. An inner lumen of the shaft 102 has a diameter sufficient to receive a plurality of pre-loaded suture locking clamps 50 in their undeployed configuration. A series of the locking clamps 50 are stacked axially against each other within the tubular shaft 102 with their slots oriented toward the shaft channel 112.

FIG. 11 is an exploded perspective view of components of the side entry suture locking clamp delivery system 100. FIG. 11A is an enlarged perspective view of a proximal end of one of the side entry suture locking clamps 50, while FIG. 11B shows a stacked series 116 of the clamps from a distal end as would be loaded into the delivery system 100.

The clamp delivery system 100 includes the aforementioned exterior shaft 102, a series of the stacked locking clamps 50, an elongated retention pin or cable 120, and an inner pusher tube 122 that slides within the lumen of the shaft 102. As seen in the sectional views of FIGS. 12A and 12B, the retention cable 120 extends through a lumen within the pusher tube 122 to the distal end of the shaft 102 and is positioned within the distal most suture locking clamp 50. The retention cable 120 performs the same function as the aforementioned retention pin 70 described above with reference to a single locking clamp 50. That is, the common retention cable 120 extends through the series of locking clamps 50, maintaining each of them in its undeployed configuration. At the same time, the retention cable 120 holds the series of locking clamps 50 within the system 100. To enhance release of each suture locking clamp 50, a small raised area 124 (see FIG. 11A) may be provided on one end of each half of the clamp to separate the clamps from each other, as seen in FIG. 12B. These raised areas 124 of the proximal most clamp 50 are received within a stepped bore 126 in the distal end of the pusher tube 122.

In one embodiment, the retention cable 120 and pusher tube 122 are displaced axially by a movement mechanism (not shown) within the proximal handle 104. As will be described in more detail below, the movement mechanism is configured to retract the cable 120 proximally relative to the tube 122, and advance the cable 120 and tube 122 together distally within the shaft 102. For example, depression of the trigger 108 retracts the retention cable 120 within the pusher tube 122, and release of the trigger urges both the retention cable 120 and pusher tube 122 distally within the shaft 102. In each trigger pull and release, the retention cable 120 retracts within the pusher tube 122 a distance equivalent to the axial height of one of the suture locking clamps 50, and the cable 120 and tube 122 advance the same distance.

With reference to FIG. 12B, one of the suture locking clamps 50 is shown released from the series within the shaft 102. In one embodiment, the distal most locking clamp 50, while still being retained on the retention cable 120, is located beyond the end of the shaft 102, although the locking clamp could also be partly or wholly within the shaft. In this position, the retention cable 120 extends substantially all the way through the distal most locking clamp 50, such as shown with the next locking clamp in FIG. 12B. Depression of the trigger 108 then pulls/retracts the retention cable 120 a distance equal to the height of the locking clamp 50, thus deploying the distal most locking clamp, or in other words permitting the C-clips 60 to close the slot 58 around the sutures 110. Placing the sutures 110 through the channel 112 and into the slot 58 of the distal most locking clamp 50 ensures that the locking clamp will engage the sutures when it is expelled. At this point, the surgeon releases the trigger 108 which causes axial advancement of both the tension cable 120 and pusher tube 122, thus moving the stack of locking clamps 50 and positioning the distal most clamp either outside of the shaft 102 or in a location where it can be easily released therefrom.

In a preferred embodiment, the sequence includes first proximal displacement of the retention cable 120 relative to the stack of suture locking clamps 50 and to the pusher tube 122 to activate the distalmost clamp (i.e., cause it to clamp onto the sutures 110). Subsequently, distal displacement of both the pusher tube 122 and the retention cable 120 ejects the distalmost clamp 50. This prevents ejection of a clamp 50 prior to it being deployed onto the sutures 110, thus helping to avoid fugitive clamps.

In an alternative configuration, the retention cable 126 fixedly attaches to the proximal handle 104 and thus remains with its distal end approximately even with the distal end of the shaft 102, or slightly recessed therein. Only the pusher tube 122 attaches to a movement mechanism (not shown) within the proximal handle 104. Actuation of the trigger 108 causes distal movement of the pusher tube 122 within the shaft 102. For example, actuation of the trigger 108 translates into distal movement of the pusher tube 122 equivalent to the axial height of one of the suture locking clamps 50. That is, pulling the trigger 108 causes the pusher tube 122 to push one of the pre-loaded locking clamps 50 out of the end of the shaft 102. Of course, once the suture locking clamp 50 is expelled from the end of the shaft 102, it also releases from the retention cable 120, thus causing its deployment. This configuration is slightly less desirable than the one described above because during deployment the suture locking clamps 50 move relative to the sutures 110 which are stationary. Nevertheless, the point is made that there are a number of ways to expel one suture locking clamp 50 at a time from the distal end of the shaft 102 while at the same time retracting the retention cable 120 and engaging the sutures 110 with the locking clamp.

It is important to understand that components of the various deployment tools for the suture locking clamps described herein could be modified and exchanged. That is, each of the several suture locking clamps disclosed herein includes a bifurcated clamp member defining a variable-sized slot which is biased toward a closed position. A retention member, such as the retention cable 120, maintains the slot open so that one or more sutures can be inserted into the slot, and when the retention member is removed the slot closes onto the suture(s). It should be understood that removing the retention member can be accomplished in various ways, and a preferred embodiment is an elongated tension member extending along the deployment tool and actuated from a proximal end. In the delivery system 100 the retention cable 120 defines the elongated tension member and the retention member within the clamp member 52, while in other embodiments the tension members and retention members may be separate elements.

Preferably, the outer shaft 102 is malleable or bendable into various shapes which significantly enhances the ability of a surgeon to correctly position the distal end of the system 100 as it advances toward the target location. For example, access passageways into the heart during a surgical procedure are often somewhat confined, and may not provide a linear approach to the annulus. Accordingly, the surgeon bends the shaft 102 to suit the particular surgery. Various materials and constructions may be utilized for the malleable shaft 102. For example, a plurality of Loc-Line connectors could be used which provide axial rigidity with bending flexibility. Another example is a plastic tube having a metal coil embedded therein to prevent kinking. In a preferred embodiment, an aluminum tube having a chromate (e.g., Iridite) coating is used. Aluminum is particularly well-suited for forming small tubes that can be bent without kinking, but should be coated with Iridite or the like to prevent deterioration in and reaction with the body.

Furthermore, both the retention cable 120 and the pusher tube 122 are made of flexible materials to complement the malleability of the shaft 102. For example, the retention cable 120 could be a braided wire rope or solid flexible wire. The pusher tube 122 could be made of a flexible polymer, though other materials are contemplated.

In a preferred embodiment, as seen in FIG. 13, the stacked series 116 of the side entry suture locking clamps 50 are bonded together. For instance, the raised areas 124 on the proximal end of each clamp 50 may be bonded to the flat distal surface of the adjacent clamp to form a cohesive chain. The clamps 50 may be bonded together such as by molding the locking clamp members 52 for each clamp as one long chain, with a weakened point at the junction between the raised area 124 of one clamp and the next. The C-clips 60 for each can be added after the mold step. Alternatively, the clamps 50 may be connected with adhesive at the same point which has a relatively small surface area for easy detachment, or the clamps can be snap-fit together in an interference fit. In each case, the chain of clamps 50 may be separated with a minimal amount of force. This configuration contemplates connecting two or more clamps together, and preferably the entire stack 116 of the clamps.

For instance, FIG. 14 shows one of the clamps 50 after expulsion from the distal end of the delivery system 100 showing one method of separating it from the adjacent clamp. That is, a slight twist of the outer shaft 102 should be sufficient to break the weak point between the deployed clamp 50 and the next one. The physician may need to grab and hold the deployed clamp 50 with forceps, for example. The presence of the retention cable 120 clamped within all of the other clamps 50 still within the shaft 102 should be sufficient to avoid separating more than one at a time That is, the clamps 50 in the stack 116 all compressively engage the retention cable 120 and rotate together.

The advantage of bonding or otherwise linking the clamps 50 together is that it greatly reduces the chance of losing one of the clamps 50 during a surgery. That is, prior to deploying the clamps 50 by clamping them to one or more sutures, they would be connected to each other rather than loose. The surgeon can then verify that each suture locking clamp 50 has securely engaged the sutures 110 prior to detaching it from the rest of the stack 116.

Figure 15A:
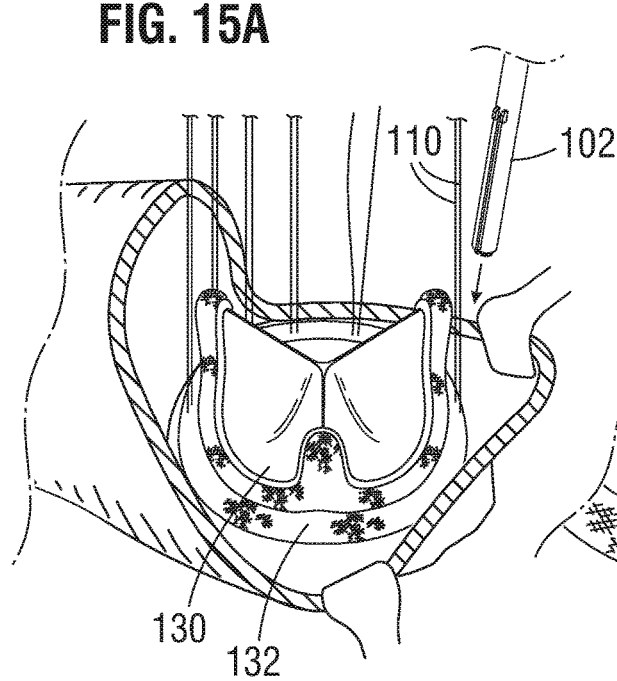
FIGS. 15A-15D are schematic views showing steps in use of the delivery system to deploy one of the side entry suture locking clamps during a prosthetic heart valve implantation procedure.

FIGS. 15A-15D show several steps in use of the delivery system 100 to deploy one of the side entry suture locking clamps 50 during a prosthetic heart valve implantation procedure. As was described with respect to FIGS. 14 and 15 above, the heart valve 130 is shown in FIG. 15A after having been advanced along an array of sutures 110 that were preinstalled at the annulus. The sutures 110 pass upward through a sewing ring 132 of the heart valve in the same positions as they are installed at the annulus. Typically, a single suture 110 passes down and up through the annulus to form a loop, and the suture pairs shown represent a single loop. The distal end of the delivery system 100 is shown advancing toward the annulus and heart valve 130 seated thereon.

Figure 15B:
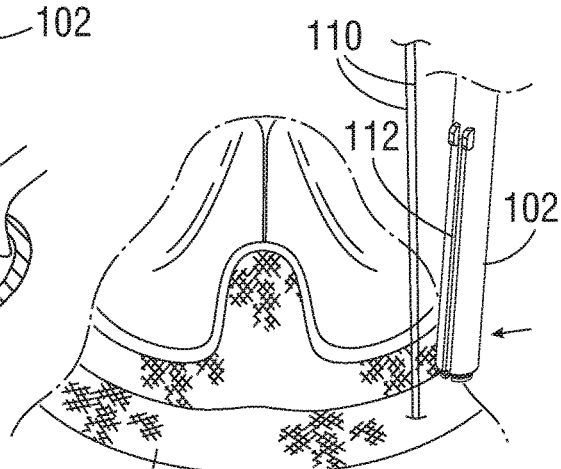
Figure 15C:
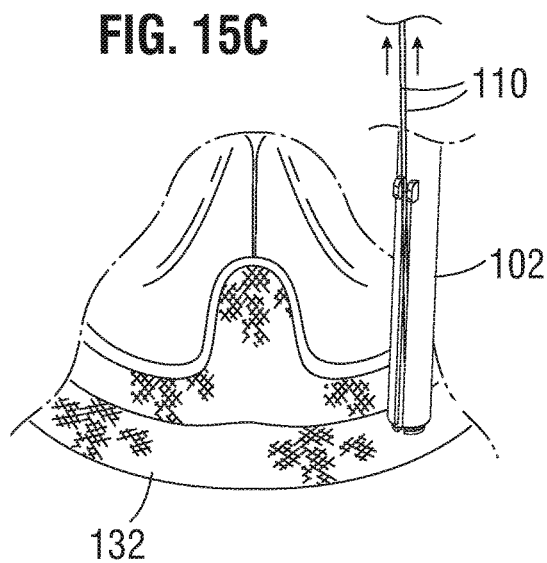
Figure 15D:
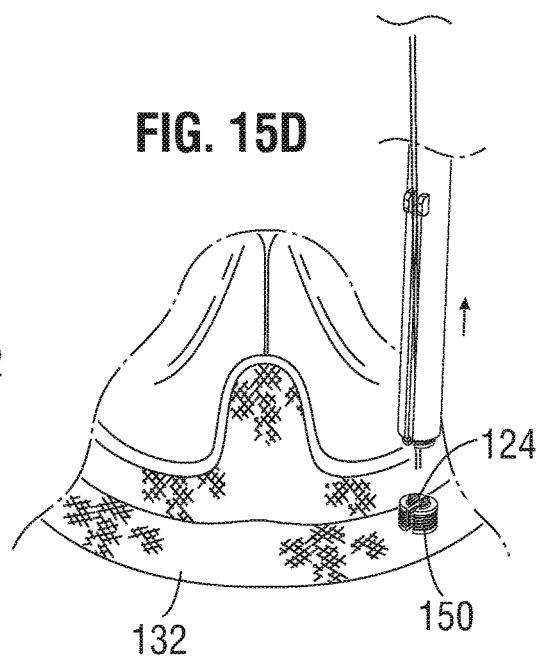

FIG. 15B is an enlarged view showing the distal end of the system 100 just prior to contact with the heart valve sewing ring 132. The pair of sutures 110 that will be secured are routed into the channel 112 on one side of the shaft 102. The shaft 102 is the advanced until its end or the distal most locking clamp 50 contacts the sewing ring, as in FIG. 15C. The suture guides 114 projecting outward from the shaft 102 help maintain the position of the sutures 110 as the surgeon pulls tension on the sutures before activating the lock, as indicated in FIG. 15C.

At this point, the surgeon activates the movement mechanism within the proximal handle 104 by pulling the trigger 108 which deploys the distal-most locking clamp 50 to clench the sutures 110, as was depicted in the detail of FIG. 12B. Momentarily, the trigger 108 remains in the fully depressed position, and the system 100 may be pulled free of the pair of sutures 110. The sutures 110 are then severed close to the clamp 50. For this purpose, a knife edge (not shown) could be incorporated into the end of the shaft 102 to facilitate cutting the suture tails after each locking clamp 50 is deployed.

The next locking clamp 50 is then positioned for deployment by releasing the trigger 108 which, as described above, simultaneously advances the tension cable 120 and pusher tube 122 by a length equal to one locking clamp. The surgeon can then reposition the distal end of the shaft 102 around the heart valve sewing ring 132 toward the next pair of sutures 110 to be secured. Because of the series of pre-loaded clamps 50 all of the pairs of sutures 110 can be secured and the valve 130 anchored to the annulus in a very short time. This greatly simplifies the use of the system and saves valuable OR time as well as on-pump time when used in open heart procedures. A less complicated and more inexpensive version could be made with a single locking clamp 50 per delivery system, which could be more practical when only 3 or so clamps needed to be used for a particular procedure, as opposed to 12-20 for a conventional surgical valve replacement.

The suture locking clamps and deployment systems disclosed herein are particularly suitable for eliminating knot-tying in surgical valve replacement, in particular for implanting a prosthetic aortic valve. They could be used with standard surgical valves where there are 10 or more pairs of sutures (e.g., 12-20), or with the EDWARDS INTUITY valve system from Edwards Lifesciences of Irvine, Calif. to eliminate the need for knot tying of three pairs of sutures located equidistantly around the sewing ring.

Despite illustration of a particular procedure, it should be understood that the presently disclosed suture locking clamps as well as instruments for deploying and securing the locking clamps are useful in other contexts than implantation of a prosthetic aortic heart valve. For example, the same suture locking clamps can be used to replace conventionally knotted sutures for prosthetic valve replacements at other native annuluses (e.g., mitral, tricuspid). Likewise, the suture locking clamps can be used to secure annuloplasty rings to any of the native annuluses. More broadly, the suture locking clamps could be used in any surgical environment in which sutures are used to secure objects or tissue in place and typically require knotting. The suture locking clamps replace the function of the suture knots, and since they are more quickly deployed they reduce the respective procedure times.

While embodiments and applications of this invention have been shown and described, it would be apparent to those skilled in the art that many more modifications are possible without departing from the inventive concepts herein, and it is to be understood that the words which have been used are words of description and not of limitation. Therefore, changes may be made within the appended claims without departing from the true scope of the invention.

What is claimed is:

1. A system for locking a device on one or more sutures, comprising:
   one or more sutures each having a thickness;
   a bifurcated locking clamp including a pair of substantially similar clamp halves each having an exterior surface with outward flanges on opposite axial ends and an inner surface facing the inner surface of the other clamp half to form a variable sized slot therebetween, the clamp halves being hinged together on a first circumferential side such that the variable sized slot defines a variable sized opening on the side opposite the first circumferential side, and such that the clamp halves are configured for pivoting movement toward or away from one another while being fixed axially with respect to one another, wherein the suture(s) extend through the slot between the inner surfaces of the clamp halves;
   a biasing member positioned on the outside of the locking clamp between the outward flanges that retain the biasing member in position, the biasing member having a relaxed size that, in the absence of an object in the slot, urges the inner surfaces of the clamp halves together such that the slot has a width smaller than the suture thickness; and
   a retention member positioned between the clamp halves against the force of the biasing member and having a thickness that maintains the slot width large enough to permit passage of the suture therethrough, wherein removal of the retention member permits the biasing member to urge the inner surfaces of the clamp halves together and clamp the suture(s) therebetween.

2. The system of claim 1, wherein a maximum radial dimension of the bifurcated locking clamp is about 2 mm or less.

3. The system of claim 1, wherein the biasing member comprises a plurality of C-clips arranged around the locking clamp with their free ends located on either side of the variable sized slot opposite the first circumferential side.

4. The system of claim 1, wherein the clamp halves are molded from a single piece of material with a living hinge on the first circumferential side.

5. The system of claim 1, wherein the inner surfaces of the clamp halves possess features to create one-way friction between the clamp halves and the suture(s).

6. The system of claim 5, wherein the features between the clamp halves and the suture(s) comprise a plurality of grip members provides on the inner surfaces of each clamp half.

7. The system of claim 6, wherein the grip members are formed as wedges with a ramp angled in one axial direction.

8. The system of claim 6, wherein the grip members are axially offset on the two clamp halves.

9. A system for locking a device onto at least one suture having a thickness, comprising:
   an elongated delivery tool having a proximal end, a distal end, and a delivery tube therebetween having a lumen, the tool further including an elongated tension member that extends along the delivery tube;
   a suture locking device positioned on the distal end of the delivery tool having a bifurcated locking clamp including a pair of substantially similar clamp halves each having an exterior surface with outward flanges on opposite axial ends and an inner surface facing the inner surface of the other clamp half to form a variable sized slot therebetween, the clamp halves being hinged together on a first circumferential side such that the variable sized slot defines a variable sized opening on the side opposite the first circumferential side, and such that the clamp halves are configured for pivoting movement toward or away from one another while being fixed axially with respect to one another, wherein the device further includes a biasing member that, in the absence of an object in the slot, urges the inner surfaces of the clamp halves together such that the slot has a width smaller than the suture thickness, wherein the device has a retention member positioned between the clamp halves against the force of the biasing member with a thickness that maintains the slot width large enough to permit passage of a suture therethrough, and wherein removal of the retention member permits the biasing member to urge the inner surfaces of the clamp halves together and clamp the suture(s) therebetween, a distal end of the elongated tension member engaging the retention member to enable tension in the tension member to apply a proximal force to the retention member; and an actuator on the proximal end of the delivery tool that causes relative axial displacement between the retention member and the suture locking device so as to remove the retention member from within the variable sized slot and permit the clamp halves to clamp the suture therebetween.

10. The system of claim 9, wherein the elongated tension member and retention member are a single element defining a retention cable extending through multiple suture locking devices arranged in series within the delivery tube.

11. The system of claim 10, wherein the actuator on the proximal end of the delivery tool proximally retracts the retention cable relative to the series of suture locking devices.

12. The system of claim 11, wherein the actuator proximally retracts the retention cable from between the clamp halves of just a distal most clamp to deploy the distal clamp onto the suture.

13. The system of claim 11, further including a pusher tube located within the delivery tube and in contact with a proximal suture locking device in the series of suture locking devices, and further wherein the actuator alternately causes distal displacement of both the pusher tube and the retention cable, and then proximal displacement of the retention cable relative to the series of suture locking devices and to the pusher tube.

14. The system of claim 10, wherein the locking clamps are bonded together in the series with a weak point therebetween to enable separation of a deployed clamp from the stack.

15. The system of claim 10, wherein the biasing members comprise a plurality of C-clips arranged around respective locking clamps with free ends located on either side of the variable sized slot.

16. The system of claim 15, wherein the delivery tube has a longitudinal channel commencing at a distal tip and extending a distance axially along the tube, the series of locking clamps being oriented so that their variable sized slots are all aligned with the longitudinal channel to permit side entry of a suture into one or more of the slots.

17. The system of claim 16, wherein the delivery tube further includes a pair of guides that project outward therefrom at a proximal end of and flanking the longitudinal channel to help maintain alignment of the sutures into the channel.

18. The system of claim 9, wherein the delivery tube is formed of a manually malleable material to enable bending by a surgeon, and the tension member is flexible to avoid impeding bending of the delivery tube.

19. The system of claim 9, wherein a maximum radial dimension of the bifurcated locking clamp is about 2 mm or less.

* * * * *